United States Patent [19]

Spiegler et al.

[11] Patent Number: 4,845,247
[45] Date of Patent: Jul. 4, 1989

[54] 3,4,-DIHYDRO-2H-PYRANS

[75] Inventors: Wolfgang Spiegler; Norbert Goetz, both of Worms; Manfred Sauerwald, Roedersheim-Gronau; Toni Dockner, Meckenheim; Rolf Fischer, Heidelberg, all of Fed. Rep. of Germany

[73] Assignee: Basf Aktiengesellschaft, Ludwigshafen, Fed. Rep. of Germany

[21] Appl. No.: 76,612

[22] Filed: Jul. 23, 1987

[30] Foreign Application Priority Data

Aug. 22, 1986 [DE] Fed. Rep. of Germany ....... 3628576

[51] Int. Cl.$^4$ ........................................... C07D 309/22
[52] U.S. Cl. ................................... 549/427; 549/425; 549/428
[58] Field of Search ....................... 549/427, 425, 428

[56] References Cited

FOREIGN PATENT DOCUMENTS 3507378 9/1986 Fed. Rep. of Germany .

OTHER PUBLICATIONS

Houben-Weyl, Methoden der Organischen Chemie, Bd 614 1966, p. 85.
Journal of Organic Chemistry 44, 366 (1979).

Primary Examiner—Nicky Chan
Attorney, Agent, or Firm—John H. Shurtleff

[57] ABSTRACT 3,4-dihydro-2H-pyrans I

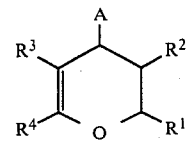

where $R^1$, $R^2$, $R^3$ and $R^4$ are each H or $C_1$–$C_6$-alkyl and $R^3$ is not $C_2$–$C_4$-alkyl when A is $COOR^5$, and A is $COOR^5$, $=CHOR^5$, in which $R^5$ is $C_1$–$C_4$-alkyl, or $CH_2OR^6$, in which $R^6$ is $C_1$–$C_4$-alkyl or is benzyl which is unsubstituted or substituted by $C_1$–$C_4$-alkyl, alkoxy or halogen, or is formyl, $C_2$–$C_4$-alkylcarbonyl or benzoyl which is unsubstituted or substituted by $C_1$–$C_4$-alkyl, alkoxy or halogen, are prepared by eliminating an alcohol from a 2-alkoxytetrahydropyran II

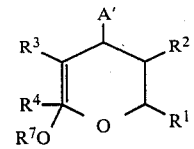

where $R^7$ is $C_1$–$C_{18}$-alkyl and A' is $COOR^5$, $CH(OR^5)_2$ or $CH_2OR^6$, in which $R^5$ and $R^6$ have the meanings stated for I, the elimination being carried out by passing II, in the liquid or gaseous state, into a high boiling mineral oil at above the boiling point of the resulting dihydropyran I, removing I in gaseous form, replenishing the high boiling mineral oil when it becomes enriched with byproducts, and removing the said mineral oil enriched with byproducts.

2 Claims, 1 Drawing Sheet

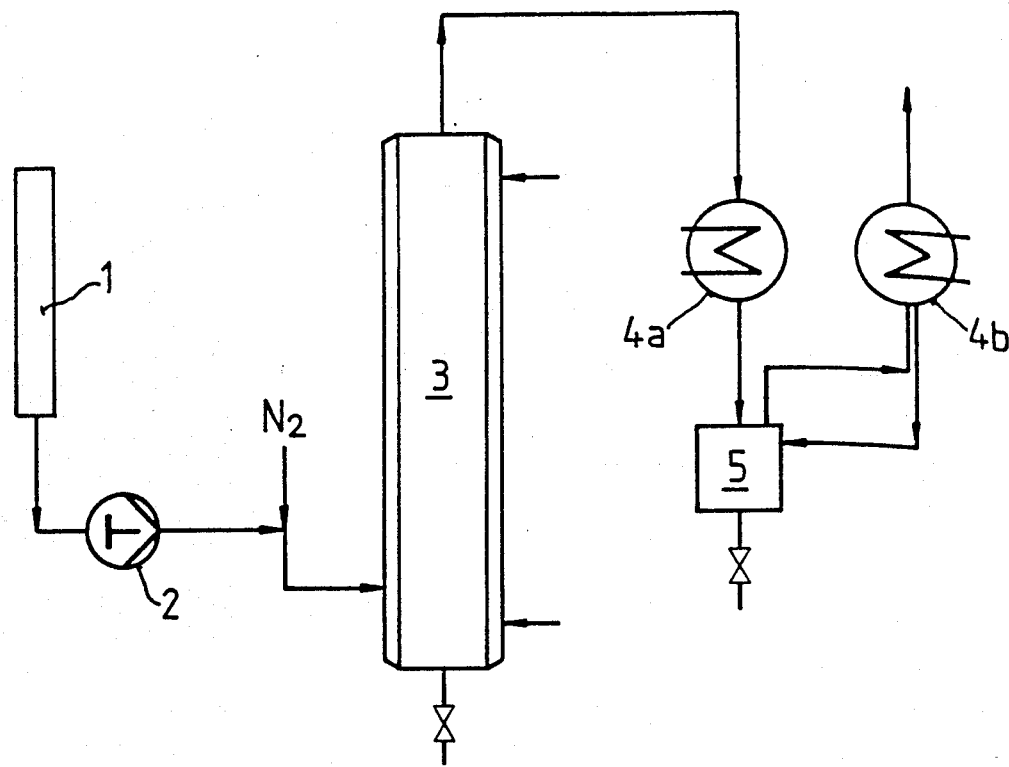

3,4,-DIHYDRO-2H-PYRANS

The present invention relates to novel 3,4-dihydro-2H-pyrans which are prepared by by eliminating an alcohol from a 2-alkoxytetrahydropyran.

In the prior art, for example Houben-Weyl, Methoden der organischen Chemie, vol. 6/4, 1966, pages 85, 3,4-dihydropyrans are obtained by heating 2-alkoxytetrahydropyrans in the presence of strong acids or phosphorus pentoxide in the liquid phase, with elimination of alcohols. As a rule, the temperatures are from 130° to 200° C. Because of these drastic conditions, substantial amounts of byproducts are formed, for example by isomerization and polymerization of the dihydropyran formed, resulting in substantially reduced yields.

J. Org. Chem. 44 (1979) 366 describes a particularly mild process for the preparation of 3,4-dihydropyrans. In this process, the 2-alkoxytetrahydropyran is heated to about 160° C. in the presence of a catalytic amount of p-toluenesulfonic acid, and the reaction products alcohol and dihydropyran are isolated by distillation. However, where starting materials having acid-sensitive radicals are reacted, even this process is unsatisfactory; for example, when 2-methoxy-4-dimethoxymethyltetrahydropyran is used as a starting material, a complex reaction mixture containing a large number of byproducts (see Comparative Example 4) is obtained even before complete conversion has been achieved.

It is an object of the present invention to provide 3,4-dihydro-2H-pyrans having a substitution pattern unknown to date, in particular possessing acid-sensitive radicals, and in doing so to follow an advantageous synthesis route.

We have found that this object is achieved by 3,4-dihydro-2H-pyrans of the general formula I

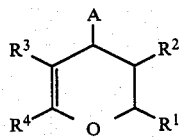

where $R^1$, $R^2$, $R^3$ and $R^4$ are identical or different and are each hydrogen or $C_1$–$C_6$-alkyl and A is $COOR^5$ or $=CH-OR^5$, in which $R^5$ is $C_1$–$C_4$-alkyl, or A is $CH_2-OR^6$, in which $R^6$ is $C_1$–$C_4$-alkyl or is aryl which is unsubstituted or substituted by $C_1$–$C_4$-alkyl or alkoxy or by halogen in the phenyl ring, or is formyl, $C_2$–$C_4$-alkylcarbonyl or benzoyl which is unsubstituted or substituted by $C_1$–$C_4$-alkyl, alkoxy or halogen, with the proviso that $R^3$ is not $C_2$–$C_4$-alkyl when A is $COOR^5$.

We have also found a process for the preparation of 3,4-dihydro-2H-pyrans of the formula I by eliminating an alcohol $R^7OH$ from a 2-alkoxytetrahydropyran of the formula II

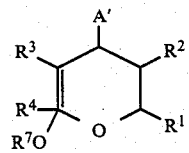

where $R^1$, $R^2$, $R^3$ and $R^4$ are identical or different and are each hydrogen or $C_1$–$C_6$-alkyl, A has the meanings stated for compound I, A' is $COOR^5$, $CH(OR^5)_2$ or $CH_2OR^6$, $R^5$ and $R^6$ each have the meanings stated for compound I and $R^7$ is $C_1$–$C_{18}$-alkyl, wherein the elimination reaction is carried out by passing the 2-alkoxytetrahydropyran II, in the liquid or gaseous state, into a high boiling mineral oil at above the boiling point of the resulting 3,4-dihydropyran I, the dihydropyran I is removed in gaseous form, the high boiling mineral oil is replenished when it becomes enriched with byproducts, and the said mineral oil enriched with byproducts is removed.

The radicals $R^1$, $R^2$, $R^3$ and $R^4$ stated for compounds I and accordingly for starting materials II are each, independently of one another, hydrogen or branched or straight-chain $C_1$–$C_6$-alkyl, eg. methyl, ethyl, propyl, isopropyl, butyl, isobutyl, tert-butyl, pentyl, 3-methylbutyl or hexyl.

The radical A in formula I is a functional group $COOR^5$, $=CH-OR^5$ or $CH_2-OR^6$, where $R^5$ is $C_1$–$C_6$-alkyl and $R^6$ has the same meanings as $R^5$ and is moreover benzyl which is unsubstituted or substituted in the phenyl ring by $C_1$–$C_4$-alkyl, alkoxy or halogen, eg. fluorine, chlorine or bromine. Examples are o-methylbenzyl, p-methoxybenzyl, p-butoxybenzyl, ortho- or para-chloro- or bromobenzyl. $R^6$ is furthermore formyl, $C_2$–$C_4$-alkylcarbonyl, eg. acetyl or propionyl, or benzoyl which is unsubstituted or substituted by $C_1$–$C_4$-alkyl, alkoxy or halogen, eg. chlorine or bromine.

Examples of radicals A are methoxycarbonyl, ethoxycarbonyl, propoxycarbonyl, isopropoxycarbonyl, butoxycarbonyl, methoxy-, ethoxy-, propoxy-, butoxy- and tert-butoxymethylidene, methoxymethyl, ethoxymethyl, propoxymethyl, isopropoxymethyl, butoxymethyl, isobutoxymethyl, tert-butoxymethyl, benzyloxymethyl, formyloxymethyl, acetoxymethyl, propionyloxymethyl, benzoyloxymethyl, 4-methylbenzoyloxymethyl, 4-methoxybenzoyloxymethyl and 4-chlorobenzoyloxymethyl.

In starting material II, A' is $COOR^5$ or $CH_2-OR^6$, where $R^5$ and $R^6$ have the meanings stated for I, or, instead of the radical $=CH-OR^5$ in I, is the radical $CH(OR^5)_2$, eg. dimethoxymethyl, diethoxymethyl, dipropoxymethyl or dibutoxymethyl.

Suitable radicals $R^7$ in formula II are $C_1$–$C_{18}$-alkyl, in particular $C_1$–$C_8$-alkyl, preferably $C_1$–$C_4$-alkyl. $R^7$ is, for example, methyl, ethyl, propyl, isopropyl, butyl, isobutyl, tert-butyl, pentyl, 2-methylbutyl, hexyl, 2-methylpentyl, heptyl, octyl, 2-ethylhexyl, isooctyl, nonyl, isononyl, decyl, isodecyl, 3,5,5,7-tetramethylnonyl, isotridecyl, pentadecyl, hexadecyl or octadecyl. Isooctyl, isononyl, isodecyl and isotridecyl are trivial names and originate from the alcohols obtained by the oxo synthesis (cf. Ullmann, Enzyklopädie der Technischen Chemie, 4th edition, volume 7, pages 216 and 217, and volume 11, pages 435 and 436).

Preferred 3,4-dihydro-2H-pyrans I are those in which $R^1$, $R^2$, $R^3$ and $R^4$ are each hydrogen or methyl and A is methoxycarbonyl, methoxymethylidene, methoxymethyl, tert-butoxymethyl, benzyloxymethyl or acetoxymethyl. When A is $COOR^5$, $R^3$ is preferably propyl, pentyl or hexyl and in particular methyl or hydrogen.

The 2-alkoxytetrahydropyrans II required for the novel process can advantageously be prepared by the process described in the earlier application P No. 35 36 956.6 (U.S. application Ser. No. 06/925,362) of Oct. 17, 1985.

The conversion of II to 3,4-dihydropyrans I is carried out, according to the invention, by a process described in general terms for open-chain as well as cyclic acetals in the earlier application P No. 35 07 378.0 (EP No. 86 102 621.9) of Mar. 2, 1985. The only cyclic acetals stated are 2,5-dimethoxy-2,5-dihydrofurans. The elimination of methanol leads to the aromatic furan system.

The elimination reaction is advantageously carried out without the use of a catalyst, ie. purely thermally by passing the 2-alkoxytetrahydropyran II, in the liquid or gaseous state, into a high boiling mineral oil, eg. gas oil, vacuum gas oil, heavy fuel oil, industrial white oil or vacuum residues. The reaction temperatures are above the boiling point of the resulting dihydropyran I and are in general from 50° to 600° C., preferably from 50° to 550° C., in particular from 150° to 350° C.

In general, atmospheric or superatmospheric pressure is used, but it is also possible to carry out the reaction under reduced pressure. Furthermore, the catalysts stated in the earlier application can be added in small amounts, although this tends to be disadvantageous since it may favor side reactions.

Examples of suitable reactors for the elimination reaction are stirred kettles. However, vertical cylindrical reactors, such as bubble tray columns, bubble columns or packed columns, are advantageously used for the process. The tetrahydropyrans II are as a rule fed in gaseous or liquid form to the bottom of the reactor filled with mineral oil. It may be advantageous to dilute the vaporized starting material II with an inert gas. Examples of suitable inert gases are steam, carbon dioxide and, preferably, nitrogen.

The 3,4-dihydro-2H-pyrans I formed are removed in gaseous form at the top of the reactor. The gaseous products are then advantageously condensed. The condensation may be followed by a purification stage, for example distillation or fractionation.

The novel process may be carried out batchwise or continuously by a conventional technique, the continuous procedure being preferred. In the continuous procedure, it may be advantageous to feed in and remove the mineral oil continuously, for example in order to remove any byproducts formed in small amounts, such as polymers, crack products or fairly high boiling byproducts, together with the mineral oil from the reactor. Working up and recycling the mineral oil removed is generally not economical since the mineral oil, eg. fuel oil or vacuum gas oil, is, as a rule, cheaply available. It is therefore advantageous if the mineral oil enriched with byproducts is transported for incineration, and fresh mineral oil is fed to the reactor.

The novel process has substantial advantages over that of the prior art.

No acidic catalysts are required, and starting materials having acid-sensitive radicals can therefore be converted to the dihydropyran derivatives I in high yields. Any byproducts present remain in the mineral oil, which need not be regenerated and, if necessary after removal of the catalyst, is advantageously transported to a power station.

The 3,4-dihydro-2H-pyran derivatives I obtainable by the novel process are useful intermediates for the synthesis of drugs, dyes and in particular crop protection agents, for example herbicides having the cyclohexane-1,3-dione skeleton, as described in German Laid-Open Application DOS No. 3,121,355 or its equivalent U.S. Pat. No. 4,422,864. After conversion of the group A to the desired functionality, for example to a hydroxymethyl, aldehyde or carboxyl group, by a conventional method, the intermediates can be bonded directly to the cyclohexanedione system (cf. U.S. Pat. No. 4,422,864).

The Examples which follow illustrate the invention.

EXAMPLES 1–3

In an apparatus as shown in FIG. 1, 60 g/hour of starting material II were fed in liquid form from a stock vessel 1 by means of a metering pump 2 via a capillary tube to the reactor 3, together with 200 l/h of nitrogen. The reactor consisted of a double-walled tube having a length of 1.25 m and a diameter of 60 mm. It was filled with 1700 g of vacuum gas oil of boiling point 350° C. The reaction temperature was 200° C. The vapors leaving the reactor were condensed in condensers 4a and 4b and collected in discharge container 5. In order to remove resulting byproducts, eg. polymers, from the reactor, 100 g/hour of vacuum gas oil were removed from the bottom outlet valve and replaced by 100 g/hour of fresh oil.

The results of the experiments are summarized in Table 1. The products formed were obtained in a purity of more than 98% by fractional distillation.

TABLE 1

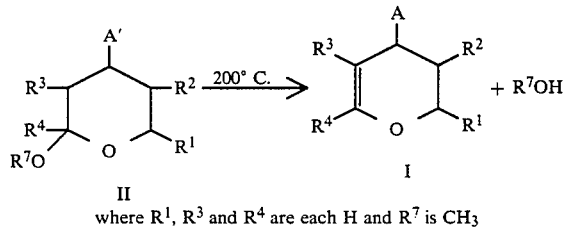

where $R^1$, $R^3$ and $R^4$ are each H and $R^7$ is $CH_3$

| | Starting material II | | Amount of II/h | Amount discharge | I in discharge | | $CH_3OH$ in discharge | Yield of I %, based on | Boiling point | |
|---|---|---|---|---|---|---|---|---|---|---|
| Example | $R^2$ | A' | mole | g | A | % by wt. | % by wt. | II | 0° C. | mbar |
| 1 | H | $CO_2CH_3$ | 0.34 | 56 | $CO_2CH_3$ | 81.6 | 18.4 | 93 | 68–72 | 10–13 |
| 2 | H | $CH(OCH_3)_2$ | 0.32 | 52 | $=CHOCH_3$ | 66.3 | 33.7 | 87 | 56–62 | 28 |
| 3 | $CH_3$ | $CH_2OOCCH_3$ | 0.32 | 54 | $CH_2OOCCH_3$ | 84.2 | 15.8 | 90 | 96–100 | 10 |

EXAMPLE 4

(Comparative Example for Example 2)

A mixture of 5.0 g (26 moles) of 2-methoxy-4-dimethoxymethyltetrahydropyran and 0.02 g (0.13 mole) of p-toluenesulfonic acid was added dropwise to a flask heated at 150° C. At the same time, 4.4 g of the resulting product mixture were distilled off under 200 mbar, a gas chromatographic amount of the said mixture having the following composition: 60% of 2-methoxy-4-dimethoxymethyltetrahydropyran, 19% of 4-methoxymethylidene-3,4-dihydro-2H-pyran and about 10 different by-products whose structure was not determined (together 21%).

We claim:

1. A 3,4-dihydro-2H-pyran of the formula

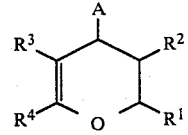

where $R^1$, $R^2$ $R^3$ and $R^4$ are identical or different and are each hydrogen or $C_1$–$C_6$-alkyl, and A is $=CH-OR^5$ in which $R^5$ is $C_1$–$C_4$-alkyl.

2. The compound of the formula

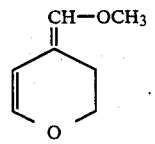

* * * * *